(12) United States Patent
Shin

(10) Patent No.: US 7,767,016 B2
(45) Date of Patent: Aug. 3, 2010

(54) COATING SOLUTION COMPOSITION OF PHOTO-ALIGNMENT MATERIAL

(75) Inventor: Dong Cheon Shin, Seoul (KR)

(73) Assignee: LG. Display Co., Ltd., Seoul (KR)

( * ) Notice: Subject to any disclaimer, the term of this patent is extended or adjusted under 35 U.S.C. 154(b) by 321 days.

(21) Appl. No.: 11/431,756

(22) Filed: May 10, 2006

(65) Prior Publication Data

US 2007/0003708 A1 Jan. 4, 2007

(30) Foreign Application Priority Data

Jun. 30, 2005 (KR) .................. 10-2005-0058001

(51) Int. Cl.
- B05D 3/10 (2006.01)
- B05D 3/14 (2006.01)
- C09K 19/54 (2006.01)
- G02F 1/1337 (2006.01)

(52) U.S. Cl. .............. 106/287.21; 252/299.4; 428/1.2; 349/123

(58) Field of Classification Search ............ 428/1.2, 428/1.25, 1.26; 252/299.4; 106/287.21; 349/123
See application file for complete search history.

(56) References Cited

U.S. PATENT DOCUMENTS

| | | | |
|---|---|---|---|
| 5,496,584 A * | 3/1996 | Yanagimoto et al. | 427/154 |
| 7,074,344 B2 * | 7/2006 | Nakata et al. | 252/299.4 |
| 2003/0087045 A1 * | 5/2003 | Nakata et al. | 428/1.27 |
| 2004/0257510 A1 * | 12/2004 | Chae | 349/141 |
| 2005/0099571 A1 * | 5/2005 | Hong et al. | 349/141 |

* cited by examiner

Primary Examiner—Shean C Wu
(74) Attorney, Agent, or Firm—Brinks Hofer Gilson & Lione

(57) ABSTRACT

There is provided a coating solution composition of a photo-alignment material. The coating solution composition of the photo-alignment material, adaptive for a photo-alignment process, employs a imidazolidinone-based solvent instead of a typical NMP-based solvent. In a coating method, the photo-alignment material is coated on a substrate in a state that its structure is stabilized in the coating solution through optimization of the coating solution composition. Accordingly, the photoreaction yield increases and a reaction product is stabilized so that a twist angle and a pretilt angle can be improved.

27 Claims, 4 Drawing Sheets

| mixing ratio | 3:7 | 4:6 | 5:5 | 6:4 |
|---|---|---|---|---|
| twist angle | 90 | 90 | 89 | 88 |

MIXING RATIO = DMI : BC

Dimethylimidazolidinone (DMI)

Dipropylimidazolidinone (DPI)

Diethylimidazolidinone (DEI)

COATING SOLUTION COMPOSITION OF PHOTO-ALIGNMENT MATERIAL

PRIORITY CLAIM

This application claims benefit of priority to Korean Patent Application No. P2005-058001, filed Jun. 30, 2005, the disclosure of which is hereby incorporated by reference.

TECHNICAL FIELD

The present invention relates to a photo-alignment material used as an alignment layer and method of use in a non-rubbing process, and more particularly, to a coating solution composition for a photo-alignment material capable of maximizing characteristics of a photo-alignment agent.

DESCRIPTION OF THE RELATED ART

In recent years, as a liquid crystal display device (LCD) has been widely and popularly used for a wall mounted TV, a high definition TV (HD-TV), and so forth, as well as a calculator, a notebook computer, etc, there is required an LCD with high quality, high definition and wide viewing angle.

Generally, the LCD is configured with two glass substrates coated with alignment layers, and a liquid crystal layer sandwiched therebetween. If an electric field is applied to the LCD from an exterior, liquid crystal molecules are rearranged so that a desired image is displayed. At this time, it is essential to uniformly align the liquid crystal in a specific direction in order to obtain uniform brightness and high contrast ratio.

Currently, a rubbing process and a non-rubbing process such as a silicon oxide oblique direction deposition process, a liquid crystal alignment inducing process using an ion beam, a photo-alignment process, and the like, are known processes for aligning the liquid crystal.

FIG. 1 is a schematic diagram illustrating an alignment process of a liquid crystal alignment layer according to a related art rubbing process.

Referring to FIG. 1, according to the related art rubbing process, a polymer compound such as polyimide or the like is coated on a substrate 2 first. Thereafter, a rubbing drum 7 rotates at a high speed to rub the surface of the coated substrate 2 so that microgrooves are formed on the surface of the polymer compound. Herein, the rubbing drum 7 is rolled up in a predetermined cloth with nylon or polyester rayon.

Through the rubbing process, the liquid crystal molecules are aligned at a predetermined pretilt angle on the surface of the alignment agent. Meanwhile, since the rubbing process has advantages that the process is simple and adaptive for scaling up the device with high-speed performance, it is widely used industrially.

However, the microgroove formed in the alignment layer may have a different shape according to a friction strength between an alignment cloth and an alignment layer 1. As a result, the alignment of the liquid crystal molecule is not uniform so that there occur phase distortion and light scattering. Moreover, the substrate 2 may be damaged due to electrostatic discharge (ESD) which is generated while rubbing the surface of the polymer. Further, there is a problem that a production yield decreases due to the micro dust generated from the rubbing drum 7.

In addition, in case of fabricating a multi-domain display device for securing a wide viewing angle in which one pixel is divided into several small pixels and a liquid crystal in each small pixel is differently aligned, there are required a complicated lithographic process such as alignment layer coating, rubbing, photoresist coating, exposure/development, rubbing, photoresist removal, etc. Therefore, this complicated process is not adaptive for the multi-domain display device from the standpoint of productivity and cost.

Alternatively, a photo-alignment process is a non-rubbing, non-contact process. In detail, a linearly polarized ultraviolet (UV) ray is vertically or slantly irradiated on a substrate coated with photosensitive polymer to induce photo-dimerization or photo-isomerization. Accordingly, there is formed an anisotropy on the surface of the polymer.

A photo-alignment process has been described using azo benzene compounds (K. Ichimura et al., Langmuir, 4, 1214, 1988). Whereafter, various kinds of polymer compound such as polymaleimide (H. J. Choi et al., U.S. Pat. No. 6,218,501), polyolefin (R. H. Herr et al., U.S. Pat. No. 6,201,087), or the like, have been developed.

In the photo-alignment process using a liquid crystal alignment agent, the liquid crystal alignment agent has a predetermined direction with respect to a polarization direction of the linearly polarized UV ray, which is mainly determined by the structure of the photosensitive polymer that will be used. Furthermore, a pretilt direction is varied with the incident direction of the irradiated UV ray and a pretilt angle is changed by the irradiation energy and the incident angle.

Currently, the polymer most commonly-used, for example, includes an ethene group having photosensitivity. Chalcone, cinnamoyl, coumarine, or the like, is used as a photosensitizer.

In a process that forms the alignment layer by means of the aforementioned rubbing process, the alignment material for the alignment layer widely employs a polyimide-based alignment agent for fabrication process efficiency, liquid crystal alignment efficiency, and environment resistance, which are necessary conditions that the alignment agent should have.

In addition, N-methylpyrrolidone (NMP) is typically used as a solvent in a coating solution composition for coating the polyimide-based alignment agent on the substrate. This is because the polyimide alignment layer is fabricated using NMP or dimethylacetamide (DMAc) as a solute generally, and it should undergo the coating process in a polyamic acid state.

Meanwhile, since there may occur a reverse reaction in which the polyamic acid is hydrolyzed to become low molecular weight substances, it is processed after predetermined additives are added into the solution prepared without a separate purification process. Therefore, the NMP is used as a major solvent in the alignment agent for the rubbing process because it is impossible to change the solvent system of the coating solution composition, typically, the NMP used in fabricating the polyimide alignment layer.

However, the NMP has strong hygroscopic properties and the polyamic acid, which is a precursor of the polyimide, is decomposed due to moisture. Accordingly, if the NMP is used for a long time in an open system or it is stored for a long time, the molecular weight is reduced and the physical properties change.

Furthermore, according to the related art, the alignment agent, typically, the NMP used as the solvent of the polyimide alignment agent required for forming the alignment layer according to the rubbing process, is also used as the solvent of the alignment agent of the photo-alignment layer according to the non-rubbing process.

That is, since the photo-alignment process enables an anisotropy to be formed through a chemical change unlike the typical rubbing process, it is fundamentally different in principle from the system in which the anisotropy is formed through a physical method. Therefore, it is unnecessary to use the polyimide-based polymer as the alignment agent so that various types of polymer may be used as the alignment agent.

Accordingly, since the polymer fabricated as the alignment agent adaptive for the photo-alignment process is fabricated by the coating solution after it is purified through a precipitation process, there is a great need to develop a new solvent of the coating solution composition instead of the typical NMP.

SUMMARY

Accordingly, the present invention is directed to a coating solution composition of a photo-alignment material and method of use that substantially obviates one or more problems due to limitations and disadvantages of the related art.

In accordance with one aspect of the invention, as embodied and broadly described herein, there is provided a coating solution composition for a liquid crystal alignment process, the composition including an imidazolidinone-based solvent.

In accordance with another aspect of the invention, a coating solution composition of a photo-alignment material includes a dipropylimidazolidinone (DPI)-based solvent.

In accordance with yet another aspect of the invention, a method of applying a liquid crystal on a substrate includes forming a photo-alignment material on the substrate using a coating solution composition including an imidazolidinone-based solvent.

In accordance with a further aspect of the invention, a method is provided for fabricating an LCD device including first and second substrates having an alignment layer on the first and second substrates, and a liquid crystal layer interposed between the first and second substrates. The method includes using a coating solution composition in an alignment material that is adapted for use in an alignment process, where the coating solution composition includes an imidazolidinone-based solvent.

It is to be understood that both the foregoing general description and the following detailed description of the present invention are exemplary and explanatory and are intended to provide further explanation of the invention as claimed.

DETAILED DESCRIPTION

Figure 1:
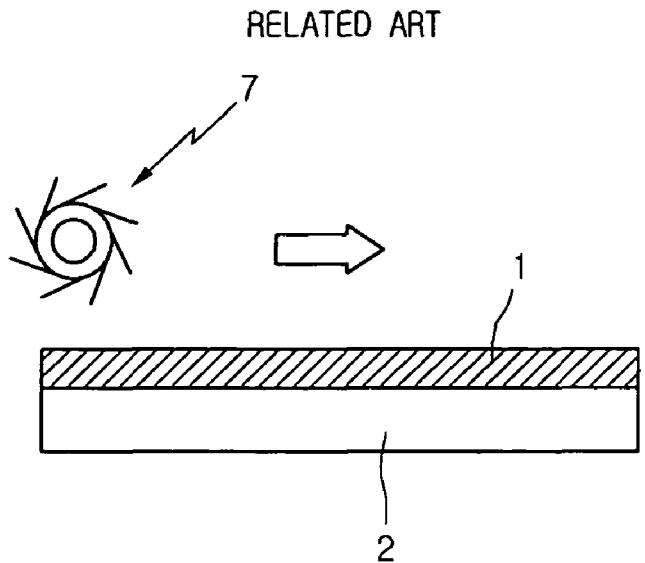
FIG. 1 is a schematic diagram illustrating an alignment process of a liquid crystal alignment layer according to a related art rubbing process.

Reference will now be made in detail to the preferred embodiments of the present invention, examples of which are illustrated in the accompanying drawings. Wherever possible, the same reference numbers will be used throughout the drawings to refer to the same or like parts.

In accordance with an aspect of the invention, 1,3 Dimethyl-2-Imidazolidinone(DMI)-based solvent is used as a solvent in a coating solution composition for an alignment agent adaptive for the photo-alignment process.

To begin with, if using the DMI-based solvent as the solvent for the alignment agent of the photo-alignment process instead of the N-methylpyrrolidone (NMP) solvent, a polymer has an optimized structure in solution because the solubility of the solvent is excellent because of an inherent characteristic of the DMI-based solvent. Accordingly, when forming an alignment layer after coating an alignment solution, the alignment layer shows more enhanced performance.

In addition, according to the present invention, since much more additives can be mixed in comparison with the typical NMP solvent because of high solubility of the DMI solvent, it is possible to enhance the quality of the coated surface.

Furthermore, as the DMI solvent has lower vapor pressure than the NMP solvent, it has such an advantageous merit that there is little change of a work environment caused by the vaporization of the solvent.

Herein, the performance of the alignment layer may be determined by an anchoring energy of the alignment layer. Because it is determined that an alignment strength of the liquid crystal improves with stonger anchoring energy, the performance of the alignment layer may be determined whether the anchoring energy is high or low. That is, as the anchoring energy becomes low, the alignment stability is deteriorated so that alignment property is degraded after a thermal process.

Besides, the anchoring energy may be measured through the changes of a pretilt angle and a twist angle of the liquid crystal. Accordingly, it is possible to indirectly predict the anchoring energy by measuring the changes of the pretilt angle and the twist angle before and after the thermal process.

Further, the twist angel is related to an azimuthal anchoring energy so that the azimuthal anchoring energy can be calculated from the measured twist angle.

The following equation illustrates how to derive a relationship between the measured twist angle and the azimuthal anchoring energy.

$$f = fb + 2fa,$$

$$fb = (\tfrac{1}{2}) K22 \, (\psi m/d)2 \, d, \text{ and}$$

$$fa = (\tfrac{1}{2}) Em \sin 2\phi m \qquad \text{[Eq. 1]}$$

$$2\phi m = \psi x - \psi m \qquad \text{[Eq. 2]}$$

minimum condition of f or df/dφm=0

$$K22(\psi m/d) = (\tfrac{1}{2}) Em \sin 2\phi m \qquad \text{[Eq. 3]}$$

$$Em = 2K22 \psi m/d \sin 2\phi m \qquad \text{[Eq. 4]}$$

where f, fb, fa, ψx, ψm, φm, Em, d, and K22 denote free energy per unit area, bulk elastic energy, surface energy, angle between rubbing direction of both substrate, actual twist angle, deviation angle, anchoring energy, cell gap, and elastic constant, respectively.

That is, in a twisted liquid crystal cell, the free energy per unit area (f) may be represented as a summation of the bulk elastic energy (fb) and the surface energy (fa), as described in Eq. 1.

Herein, ψx is the angle inducing the alignment, and ψm is an alignment angle which is actually measured.

Therefore, the deviation (φm) may be represented using a difference between ψx and ψm, as described in Eq. 2.

A direction of a director in the cell may be calculated from Eq. 3 such that the free energy per unit (f) is minimized or a differential value that f is differentiated with respect to φm becomes zero.

Accordingly, the anchoring energy (Em), which is calculated from a differential condition, df/dφm=0, may be represented like Eq. 4.

As illustrated in Eq. 4, if measuring the actual alignment angle, it is possible to calculate the anchoring energy from the difference between the actual alignment angle and the rubbing angle.

Figure 2:
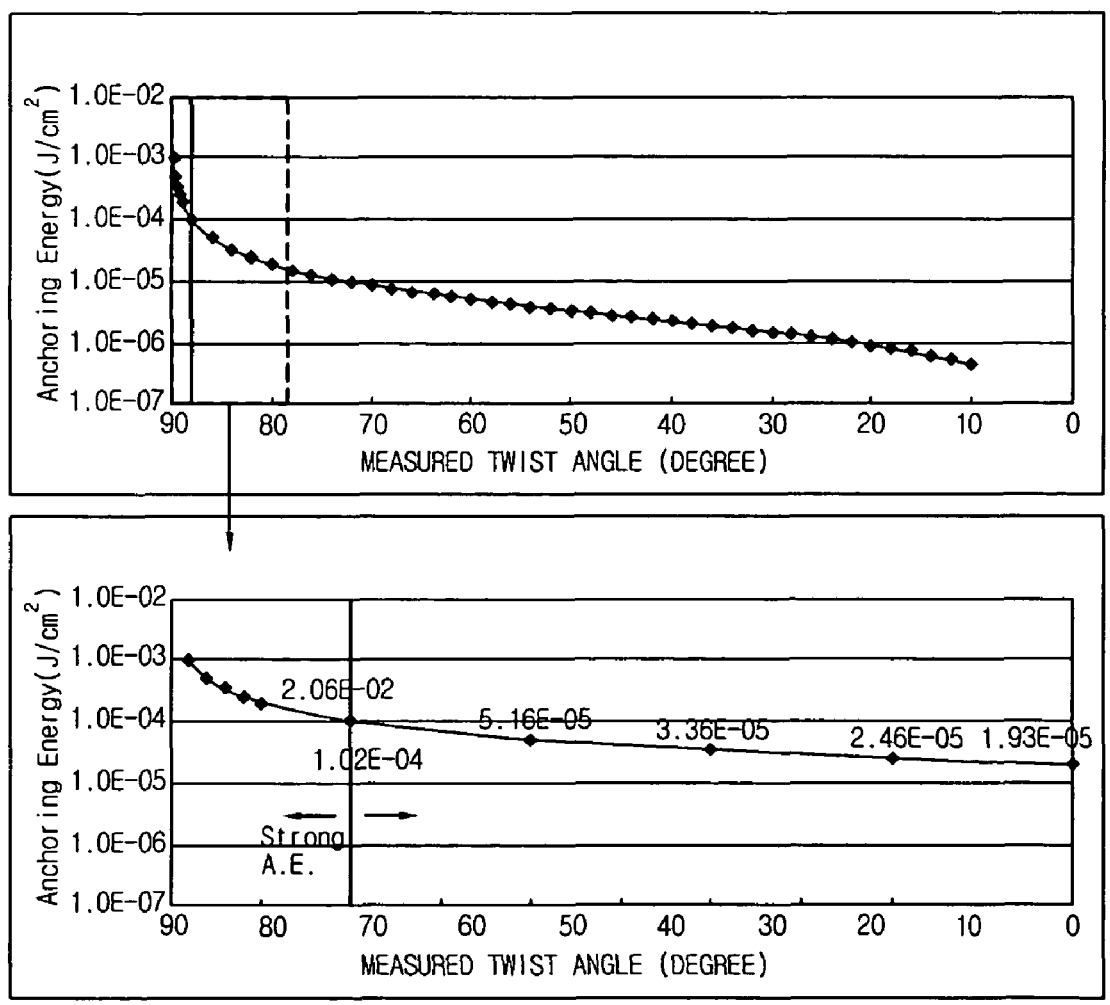
FIG. 2 is a graph illustrating a relationship between an actual twist angle of an alignment layer and an anchoring energy.

FIG. 2 is a graph illustrating a relationship between the actual twist angle of the alignment layer and the anchoring energy.

In general, if the anchoring energy has a specific value, for example, $10^{-4}$ J/m$^2$<Em<∞, it is often called a strong anchoring energy. Whereas, if the anchoring energy is less than $10^{-4}$ J/m$^2$, it is called a weak anchoring energy.

Converting the anchoring energy into the twist angle, the anchoring energy becomes higher than $10^{-4}$ J/m$^2$ if the actual alignment angle is 88° or greater in case of fabricating 90° twisted cell. Thus, it is determined that it has the strong anchoring energy.

In the present invention, the DMI-based solvent is used as the solvent for the coating solution composition of the alignment agent adaptive for the photo-alignment process, instead of the related art NMP-based solvent. Herein, the DMI-based solvent is a mixture of DMI, butyl cellosolve, butyl cellosolve acetate, and the like.

In order to maximize the twist angle of the photo-alignment agent, the mixing ratio of the DMI to the butyl cellosolve or the butyl cellosolve acetate is about 3:7 to about 5:5.

More preferably, the mixing ratio of the DMI to the butyl cellosolve or the butyl cellosolve acetate is about 3:7 to about 4:6.

Figures 3, 4A:
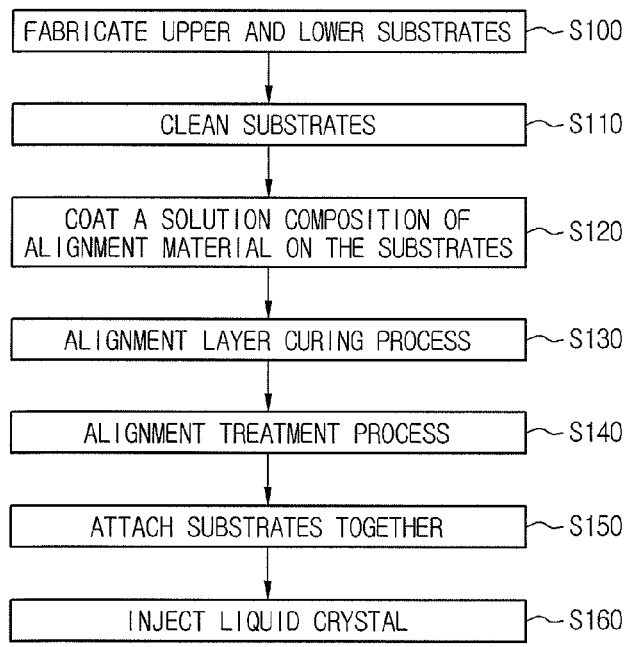
FIG. 3 is a table illustrating a relationship between a mixing ratio of a solvent as a coating solution composition for a specific photo-alignment agent and a twist angle.
FIG. 4A and FIG. 4B are flowcharts illustrating a method of fabricating an IPS LCD according to an embodiment of the present invention.

FIG. 3 is a table illustrating a relationship between a mixing ratio of a solvent as a coating solution composition for a specific photo-alignment agent and a twist angle.

As illustrated in FIG. 3, in case that the mixing ratio of the DMI to the butyl cellosolve or the butyl cellosolve acetate is 3:7 or 4:6, the twist angle is 90°, which means that the anchoring energy is very high. As a result, if using the coating solution composition according to the above mixing ratio, it is well understood from FIG. 3 that it is possible to fabricate the alignment layer with excellent performance.

As another embodiment of the present invention, a dipropylimidazolidinone (DPI)-based solvent is used as the solvent for the coating solution composition of the alignment agent adaptive for the photo-alignment process, instead of the related art NMP-based solvent. Herein, the DPI-based solvent may be a mixture of DPI, butyl cellosolve, butyl cellosolve acetate, and the like.

Figure 4B:
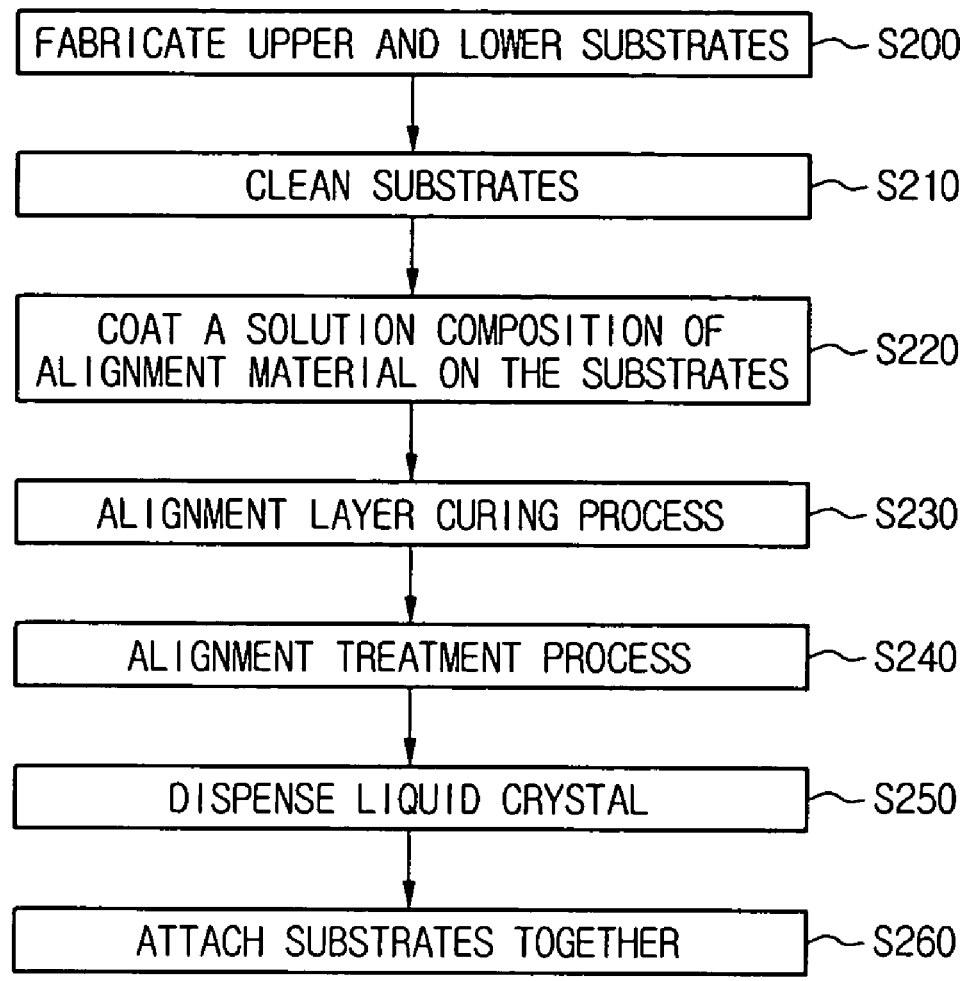
Figure 5A:
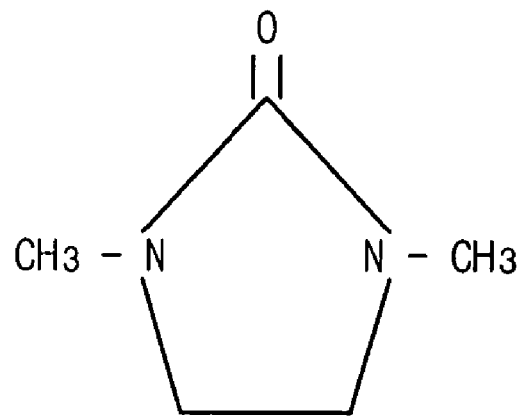
FIGS. 5A to 5C are drawings illustrating DMI, DPI, and DEI.
Figure 5B:
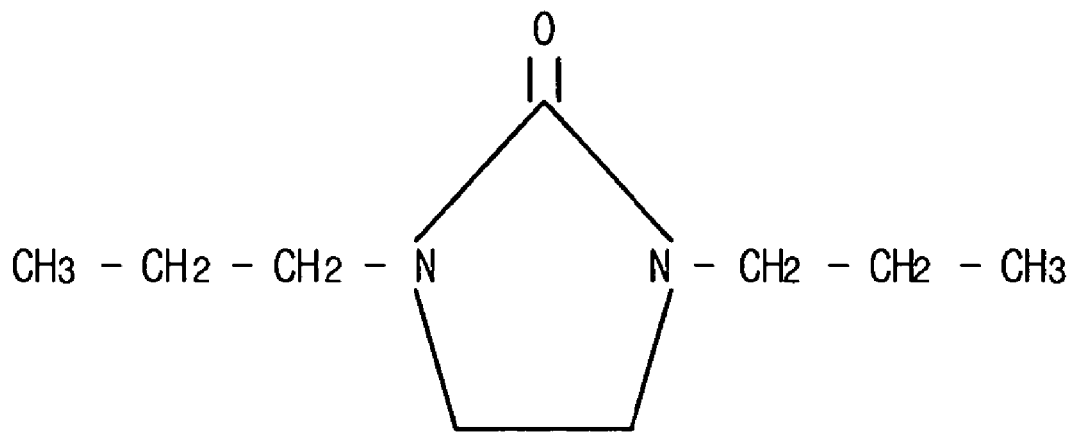
Figure 5C:
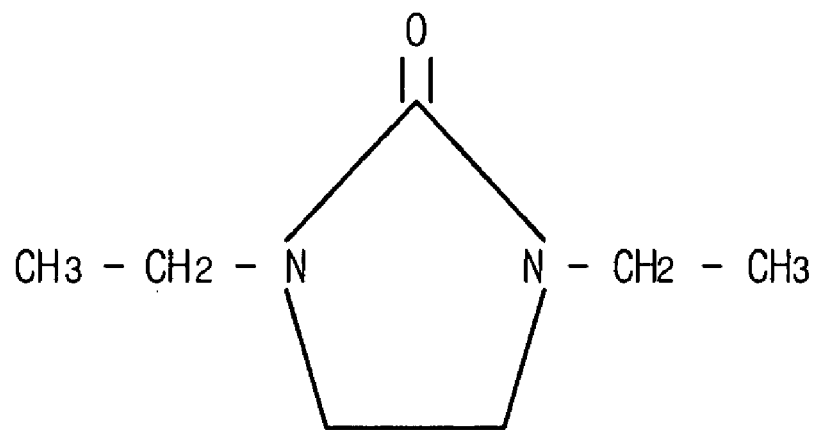

Referring to FIGS. 4A and 4B, upper and lower substrates are fabricated in Step S100 S200.

Upper and lower substrates and are attached together, and liquid crystal is provided in a space between the substrates and to form a liquid crystal layer therebetween. A metal material is deposited on the lower substrate and the resulting structure is patterned, thereby forming a plurality of ga1te lines and a gate electrode branching out from the gate line to be positioned corresponding to a TFT.

And, a black matrix for preventing a light leakage is formed on the upper substrate, and R/G/B (red/green/blue) color filter layers are formed between the black matrices.

In Step S110 S210, a cleaning process is performed to remove foreign substance on the substrates. In Step S120 S220, by using an alignment layer printing device, a coating solution composition of a photo-alignment material is printed on the substrate to form an alignment layer.

In step S130 S230, thereafter, an alignment layer curing process is performed to dry and harden a solvent of the printed coating solution composition of a photo-alignment material.

In Step S140 S240, The step S140 S240 serve to perform an alignment treatment process on the alignment layer.

The alignment treatment process could be a rubbing method or a light irradiation method.

After Step S140 S240, the upper and lower substrates are attached together, and/or a liquid crystal layer is formed in a space between the attached substrates.

In other words, after the alignment at step S140 S240, the upper and lower substrates may be attached together S150. A seal pattern serving as an adhesive may be first formed at an edge of the upper substrate, excepting a liquid crystal injection hole, and spacers are dispersed on the lower substrate. Thereafter, the upper and lower substrates are attached together at an accuracy of several micrometers for preventing light leakage. Thereafter, the attached substrates are cut into unit cells having a predetermined size. The cell cutting process includes a scribe operation of forming a line on the upper and lower substrates, and a break operation of breaking the attached substrates into unit cells by applying an impact against the scribed line. Finally, liquid crystal is injected through the injection hole into a space between the cut substrates and the injection hole is sealed S160, thereby completing the desired LCD.

Alternatively, the liquid crystal layer may be formed through a liquid crystal dispensing process. In detail, after the alignment treatment process at S240, liquid crystal is dispensed on the substrate S250, the seal pattern is formed, and then the spacers are dispersed. Thereafter, the upper and lower substrates are attached together S260, and the attached substrates are cut into unit cells, thereby completing the LCD.

Alternatively, the alignment treatment process S140 S240 could be performed after the curing process S130 S230.

Herein, the coating solution composition using the DPI according to another embodiment is similar in performance and effect to the aforementioned composition using the DMI so that further descriptions will be omitted.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. A coating solution composition for a liquid crystal alignment process, the composition comprising an imidazolidinone-based solvent,
   wherein the imidazolidinone-based solvent comprises an imidazolidinone, a butyl cellosolve and a butyl cellosolve acetate,
   wherein a ratio of the imidazolinone to the butyl cellosolve or the butyl cellosolve acetate is about 3:7 to about 5:5.

2. The coating solution composition according to claim 1, wherein the imidazolidinone is selected from a group consisting of 1,3Dimethyl-2-Imidazolidinone (DMI), Dipropylimidazolidinone (DPI), or Diethylimidazolidinone (DEI).

3. The coating solution composition according to claim 1, wherein the imidazolidinone-based solvent further comprises a γ-butyrolatone.

4. A coating solution composition for a photo-alignment material adapted for use in a photo-alignment process, the composition comprising a imidazolidinone-based solvent, wherein the imidazolidinone-based solvent comprises a mixture of an imidazolidinone and a butyl cellosolve.

5. The coating solution composition according to claim 4, wherein the imidazolidinone-based solvent further comprises a γ-butyrolatone, and a butyl cellosolve acetate.

6. The coating solution composition according to claim 4, wherein the imidazolidinone-based solvent further comprises a butyl cellosolve acetate.

7. The coating solution composition according to claim 1 further comprising a liquid crystal alignment agent configured to align in a predetermined direction with respect to a polarization direction of a linearly polarized UV light.

8. The coating solution composition according to claim 4 further comprising a liquid crystal alignment agent configured to align in a predetermined direction with respect to a polarization direction of a linearly polarized UV light.

9. A method of applying a liquid crystal on a substrate comprising forming a photo-alignment material on the substrate using a coating solution composition comprising an imidazolidinone-based solvent,
wherein the imidazolidinone-based solvent comprises a mixture of an imidazolidinone and a butyl cellosolve.

10. The method of according to claim 9, wherein the coating solution composition further comprises, a γ-butyrolatone and a butyl cellosolve acetate.

11. The method of according to claim 9, wherein the coating solution composition further comprises a butyl cellosolve acetate.

12. The method of according to claim 10, wherein the coating solution composition comprises a ratio of the imidazolidinone to one of the butyl cellosolve, the butyl cellosolve acetate or the γ-butyrolatone of about 3:7 to about 5:5.

13. The method of according to claim 9, wherein the coating solution composition further comprises a liquid crystal alignment agent configured to align in a predetermined direction with respect to a polarization direction of a linearly polarized UV light.

14. The coating solution composition according to claim 9, wherein the imidazolidinon is selected from a group consisting of 1,3Dimethyl-2-Imidazolidinone (DMI), Dipropylimidazolidinone(DPI), or Diethylimidazolidinone (DEI).

15. A method for fabricating an LCD including first and second substrates having an alignment layer on the first and second substrates, and a liquid crystal layer interposed between the first and second substrates, the method comprising using a coating solution composition in an alignment material and adapted for use in an alignment process, wherein the coating solution composition comprises an imidazolidinone-based solvent,
wherein the imidazolidinone-based solvent comprises a mixture of an imidazolidinone and a butyl cellosolve.

16. The method according to claim 15, wherein the imidazolidinone-based solvent further comprises a butyl cellosolve acetate and a γ-butyrolatone.

17. The method according to claim 15, wherein the imidazolidinone-based solvent further comprises a butyl cellosolve acetate.

18. The method according to claim 15, wherein the imidazolidinone-based solvent further comprises γ-butyrolatone.

19. The method according to claim 15, further comprising:
attaching the first and second substrates together; and
injecting liquid crystal into a space between the attached first and second substrates to form a liquid crystal layer.

20. The method according to claim 15, further comprising:
dispensing liquid crystal on one of the first and second substrates; and
attaching the first and second substrates together.

21. The method according to claim 15, further comprising:
forming a black matrix on the second substrate;
forming a color filter layer on the black matrix;
forming an overcoat layer on the color filter layer; and
forming the alignment layer on the overcoat layer.

22. The method according to claim 15, further comprising:
forming gate and common lines on the first substrate in a horizontal direction such that the gate and common lines are spaced apart from each other by a predetermined distance;
forming a data line in a direction crossing the gate line;
forming a plurality of common electrodes substantially parallel to the data line; and
forming a plurality of pixel electrodes alternating with the common electrodes.

23. The method according to claim 15, wherein the alignment layer includes an organic material having UV reactor as a solute of the coating solution.

24. The method according to claim 15, wherein the imidazolidinone is selected from a group consisting of 1,3Dimethyl-2-Imidazolidinone (DMI), Dipropylimidazolidinone (DPI), or Diethylimidazolidinone (DEI).

25. The method according to claim 15, wherein the alignment treatment process comprises a rubbing method.

26. The method according to claim 15, wherein the alignment treatment process comprises a light irradiation method.

27. The method according to claim 15, wherein the light comprises a polarized UV light or non-polarized UV or partially polarized UV.

\* \* \* \* \*